United States Patent [19]

Ueda

[11] 4,182,711
[45] Jan. 8, 1980

[54] ANTIBACTERIAL AGENTS OF THE β-LACTAM TYPE

[75] Inventor: Yasutsugu Ueda, St. Lambert, Canada

[73] Assignee: Bristol-Myers Company, New York, N.Y.

[21] Appl. No.: 900,466

[22] Filed: Apr. 27, 1978

[51] Int. Cl.² .......................................... C07D 277/00
[52] U.S. Cl. ..................................... 548/178; 424/270
[58] Field of Search ................................ 260/306.7 C

[56] References Cited

U.S. PATENT DOCUMENTS 3,950,357  4/1976  Kahan et al. .................... 260/326.27

FOREIGN PATENT DOCUMENTS 846933  4/1977  Belgium .
849118  7/1977  Belgium .
1467413  3/1977  United Kingdom .

OTHER PUBLICATIONS

Brown et al., JCS Chem. Comm., 359-360 (1977).

Primary Examiner—Nicholas S. Rizzo
Attorney, Agent, or Firm—David A. Morse

[57] ABSTRACT

There is described the preparation of novel 2-penem-3-carboxylic acid compounds having the formula

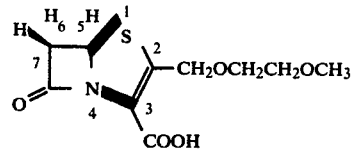

and easily cleavable esters and carboxylic acid salts thereof. The compounds of formula I, particularly the dextrorotatory isomers thereof, are potent antibacterial agents or are of use as intermediates in the preparation of such agents.

17 Claims, No Drawings

ANTIBACTERIAL AGENTS OF THE β-LACTAM TYPE

BACKGROUND OF THE INVENTION

1. Field of the Invention

The chemical processes of the present invention provide novel antibacterial agents of the β-lactam type containing a hitherto unknown nucleus and useful intermediates for the synthesis of said antibacterial agents.

2. Description of the Prior Art

Penicillins and cephalosporins comprise a group of well-known antibacterial agents commonly grouped together as a class called β-lactam antibiotics. Most of the work in this field has been done, broadly speaking, with 6-aminopenicillanic acid, 7-aminocephalosporanic acid and derivatives thereof produced by fermentation or chemical transformation of the natural products. Despite the extensive progress made in preparing active derivatives of 6-aminopenicillanic acid and 7-aminocephalosporanic acid, there is a continuing search for synthetic and semisynthetic routes to new families of β-lactam antibiotics which may possess more advantageous properties than those derived from the known penicillin and cephalosporin nuclei.

Literature publications relating to other more non-conventional β-lactam-containing antibiotics include the following:

a. Belgian Patent No. 846,933 discloses the compound of the formula

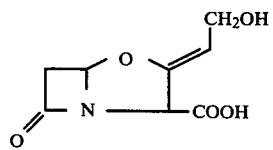

which has been isolated from fermentation of *Streptomyces clavuligerus*. This compound, named clavulinac acid, possesses a low order of antibacterial activity but inhibits the action of certain β-lactamases and reportedly enhances the in vitro and in vivo activity of some penicillins and cephalosporins.

b. U.K. Patent No. 1,467,413 discloses the fermentation product having the formula

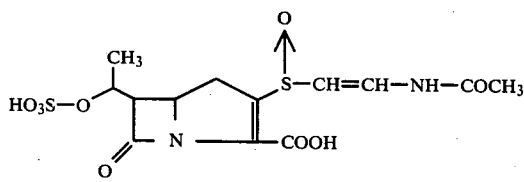

which is reported to possess some antibacterial activity and to be a β-lactamase inhibitor.

c. Brown, et al. in J.C.S. Chem. Comm., 359-360 (1977) disclose preparation of the compound of the formula

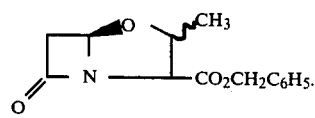

There is no indication from the publication that the compound possesses any antibacterial activity.

d. U.S. Pat. No. 3,950,357 describes a fermentation process for producing thienamycin, the compound of the formula

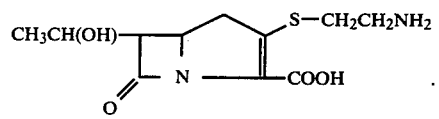

Thienamycin is reported to be a highly potent broad-spectrum antibiotic.

e. Belgian Patent No. 849,118 (equivalent U.S. Pat. No. is 4,070,477) discloses a series of 6-amino-2-penem-3-carboxylic acid derivatives of the formula

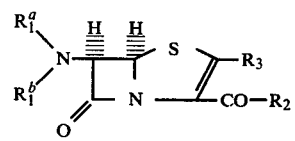

where $R_1{}^a$ is hydrogen or an N-protecting group, $R_1{}^b$ is hydrogen or acyl (or $R_1{}^a$ and $R_1{}^b$ taken together are a divalent N-protecting group), —CO—$R_2$ is carboxyl or a protected carboxyl group and $R_3$ is hydrogen or a C-bonded organic group. The compounds and their salts are said to possess antibacterial activity. No compounds are disclosed in the publication which do not contain the amino or acylamido moiety at the 6-position of the β-lactam ring.

SUMMARY OF THE INVENTION

The present invention provides a novel β-lactam compound having the formula

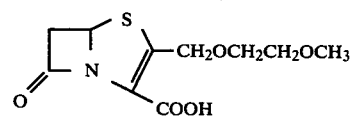

I or a pharmaceutically acceptable salt or easily cleavable ester thereof. The above compounds, including especially the dextrorotatory optical isomers thereof, are potent antibacterial agents or are intermediates useful in preparing said antibacterial agents.

Also included in this invention are various novel intermediates useful in preparing the active β-lactam derivatives described above and processes for the production of the intermediates and active compounds.

DETAILED DESCRIPTION

The compounds represented by formula I form a new β-lactam ring system. The nomenclature to be used for the compounds could be the following:

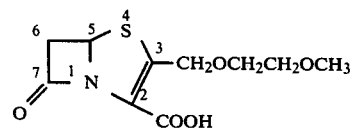

3-(2-methoxyethoxymethyl)-7-oxo-4-thia-1-azabicyclo[3,2,0]hept-2-ene-2-carboxylic acid. Alternatively, the compounds can be considered as penem derivatives and named as follows:

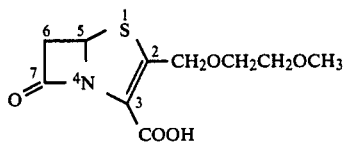

2-(2-methoxyethoxymethyl)penem-3-carboxylic acid.

The stereoconfiguration of the 2-penem compounds of the present invention may be represented as follows:

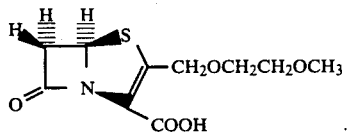

Since an asymmetric carbon atom is present (carbon 5 of the penem ring), the compounds of formula I may exist either in the form of racemic mixtures or as the individual dextrorotatory and levorotatory optical isomers. While the present invention includes both the racemic mixtures and resolved optical isomers, the preferred compounds are the dextrorotatory optical isomers (S-configuration) since these have been found to possess substantially all of the antibacterial activity attributed to the racemic mixtures.

The pharmaceutically acceptable salts referred to above include nontoxic metallic salts such as sodium, potassium, calcium and aluminum, the ammonium salts and salts with nontoxic amines such as trialkylamines (e.g. triethylamine), procaine, dibenzylamine, N-benzyl-β-phenethylamine, 1-ephenamine, N,N'-dibenzylethylenediamine, N-alkylpiperidine (e.g. N-ethylpiperidine), α-methylbenzylamine, α-ethylbenzylamine, and other amines which have been used to form salts of penicillins and cephalosporins.

Easily cleavable esters of the free acid compounds of formula I include conventional ester groups which have been used in the penicillin and cephalosporin art to block carboxyl groups, i.e., ester groups which are removable by methods which do not result in any appreciable destruction of the remaining portion of the molecule. For use as an intermediate, the preferred easily cleavable ester is the p-nitrobenzyl ester which may be removed by hydrogenolysis, e.g. catalytic hydrogenation with a noble metal catalyst. For use as biologically active compounds, physiologically cleavable esters are employed. Physiologically cleavable esters of the free acid compounds of formula I include those esters known in the penicillin and cephalosporin art to be easily cleaved within the body to the parent acid. Examples of such esters include indanyl, phthalidyl, methoxymethyl, glycyloxymethyl, phenylglycyloxymethyl, thienylglycyloxymethyl or acyloxymethyl of the formula

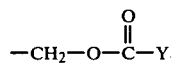

in which Y is $C_1$-$C_4$ alkyl or phenyl. Particularly preferred biologically active esters are methoxymethyl, acetoxymethyl, pivaloyloxymethyl, phthalidyl and indanyl.

It will be appreciated that the compounds of formula I may exist in various states of solvation and the anhydrous as well as solvated forms are intended to be within the scope of the invention.

The present invention further provides various novel intermediates useful in the synthesis of the compounds of formula I.

A preferred embodiment of the present invention is a novel intermediate of the formula

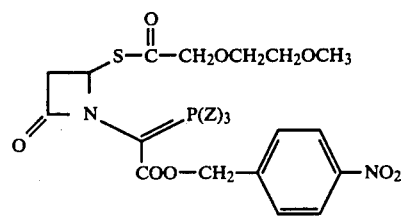

II wherein Z is phenyl or $C_1$-$C_6$ alkyl (e.g. n-butyl). The most preferred compound of formula II is that in which Z is phenyl.

Another preferred embodiment of the present invention is a novel intermediate of the formula

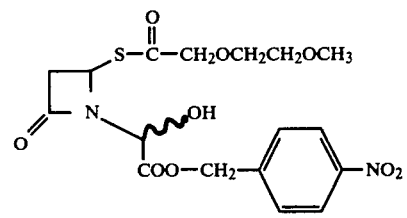

III wherein the wavy line indicates that compound III exists as a mixture of epimers.

Another preferred embodiment of the present invention is a novel intermediate of the formula

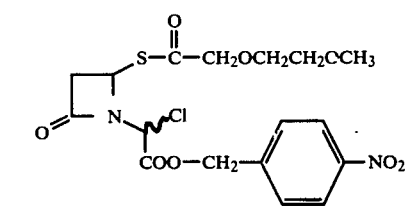

IV which exists as a mixture of epimers.

The 2-penem compounds of formula I may be prepared by the process comprising the steps of (1) thermally cyclizing in an inert organic solvent a phosphorane intermediate of the formula

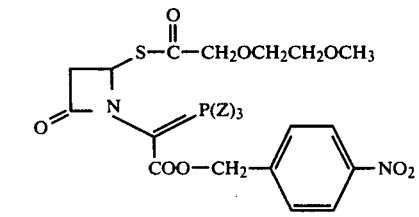

II wherein Z represents phenyl or $C_1$-$C_6$ alkyl but preferably phenyl to produce a compound of the formula

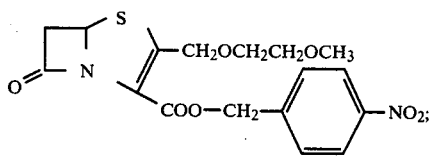 $I_a$ (2) subjecting the ester of formula $I_a$ to catalytic hydrogenation employing a noble metal catalyst in a non-reducible inert aqueous or non-aqueous solvent in the presence or absence of a base to produce the racemic acid of the formula

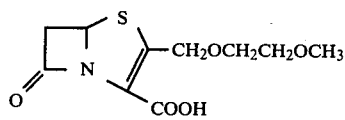 I or a carboxylic acid salt thereof and, if desired, performing one or more of the further steps selected from (a) resolving the so-produced racemic compound into its dextrorotatory and levorotatory optical isomers thereof and recovering the dextrorotatory isomer; and (b) converting the racemic free acid or salt of formula I or the dextrorotatory isomer thereof to a physiologically hydrolyzed ester thereof or a pharmaceutically acceptable carboxylic acid salt thereof.

The cyclization reaction may be carried out in an inert organic solvent or mixture of solvents such as aliphatic, cycloaliphatic or aromatic hydrocarbons (e.g. n-hexane, cyclohexane, benzene or toluene), halogenated hydrocarbons (e.g. methylene chloride, chloroform, carbon tetrachloride), ethers (e.g. diethyl ether, dioxane or tetrahydrofuran), carboxylic acid amides (e.g. dimethylformamide), di $C_1$-$C_6$ alkylsulfoxides (e.g. dimethylsulfoxide) or a $C_1$-$C_6$ alkanol (e.g. methanol, ethanol, t-butanol). Elevated temperatures are used, for example, temperatures ranging from above room temperature to the reflux temperature of the solvent system. Good results are obtained at temperatures of from about 50°–100° C.

The p-nitrobenzyl ester $I_a$ is then cleaved by hydrogenolysis in a conventional manner to give the corresponding free acid or a salt thereof. Catalytic hydrogenation may be employed with a noble metal catalyst such as palladium or rhodium, including derivatives thereof such as oxides, hydroxides or halides, said catalyst being optionally supported on a conventional carrier such as carbon or diatomaceous earth. A non-reducible aqueous or non-aqueous inert solvent such as water, methanol, ethanol, ethyl acetate, tetrahydrofuran, diethyl ether or dioxane is used for the hydrogenolysis reaction. The reaction is preferably conducted at atmospheric or slightly elevated pressure at room temperature and for a period of from about 1 to 5 hours depending on the solvent and catalyst used. If an equivalent weight of a base such as an alkali metal or alkaline earth hydroxide or an amine is employed during the hydrogenolysis, the product may be recovered in the form of a carboxylic acid salt. Alternatively, if no base is used, the free acid product is obtained.

Compound I is recovered from the hydrogenolysis step as a racemic mixture of the dextrorotatory and levorotatory optical isomers of the free acid or salt thereof. While the racemic mixture possesses potent antibacterial activity and may be employed in that form as an antibiotic agent, it has been found upon resolution of the racemate that substantially all of the antibacterial activity is in the dextrorotatory optical isomer. Accordingly, it is preferred to resolve the racemic compound I into its optical isomers by a conventional resolution procedure, e.g. by reacting the racemic acid with an optionally active amine such as α-methylbenzylamine to form diastereoisomeric salts, separating the salts and converting them into the dextrorotary and levorotatory optical isomers of free acid I. By this procedure the dextrorotatory isomer may be recovered in a form substantially free of the less active levorotatory isomer.

A racemic or resolved compound of formula I may then be converted to a pharmaceutically acceptable salt thereof or a physiologically cleavable ester thereof. Pharmaceutically acceptable salts may be formed by reaction of the acid of formula I with a suitable non-toxic base in an inert solvent and recovering the desired salt as by precipitation or lyophilization. Physiologically cleavable esters may be prepared from the racemic or resolved free acids or salts in an analogous manner to preparation of such esters of penicillins and cephalosporins.

Acyloxymethyl esters in which the 3-position of the 2-penem has the formula

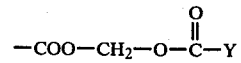

in which Y is phenyl or $C_1$-$C_4$ alkyl may be prepared by reacting an alkali metal salt of the free acid I (in the form of the racemic mixture or resolved dextrorotatory isomer), for example, the lithium, sodium or potassium salt, with an acyloxymethyl halide of the formula

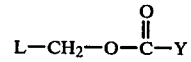

in which L is chloro or bromo and Y is $C_1$-$C_4$ alkyl or phenyl. Acyloxymethyl halides which may be employed include chloromethyl acetate, bromomethyl acetate, bromomethyl propionate, chloromethyl pivaloate, chloromethyl benzoate, and the like. The alkali metal salt of compound I is reacted in an inert solvent (e.g. tetrahydrofuran, dioxane, dimethylformamide or methylene chloride) with at least a molar equivalent of the acyloxymethyl halide at room temperature or at slightly elevated temperature, e.g. up to ~40°–45° C.

The methoxymethyl ester of compound I (racemic mixture or dextrorotatory isomer) wherein the 3-position is -COO-$CH_2OCH_3$ may be prepared by substituting for the acyloxymethyl halide in the above procedure chloromethyl methyl ether.

The indanyl ester of compound I wherein the 3-position has the formula

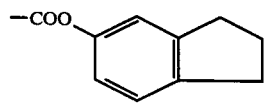

may be prepared by reacting 5-indanol in an inert solvent such as dioxane or tetrahydrofuran with the free acid form of compound I (racemic mixture or dextrorotatory isomer) in the presence of a condensing agent such as N,N'-dicyclohexylcarbodiimide.

Phthalidyl ester compounds of formula I where the 3-position has the formula

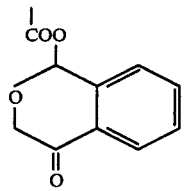

may be prepared by reacting bromophthalide having the formula

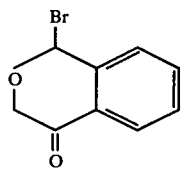

with a salt of the free acid I (racemic mixture or dextrorotatory isomer). The esterification can be carried out in an inert solvent such as dimethylformamide, dioxane or tetrahydrofuran by warming equimolar amounts of the salt of formula I, for example, the sodium or potassium salt, and bromophthalide.

The phosphorane intermediate of formula II may be prepared from 4-acetoxy-2-azetidinone, a known compound, by the following procedure:

(a) reacting 4-acetoxy-2-azetidinone of the formula

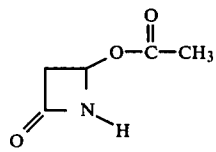

with 2-methoxyethoxythioacetic acid in an inert solvent and in the presence of a base to produce the intermediate of the formula

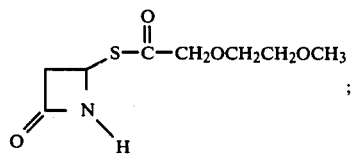

(b) reacting the above-produced intermediate with a glyoxylic acid ester of the formula

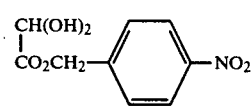

or a reactive oxo-derivative thereof such as a hydrate in an inert organic solvent, preferably at an elevated temperature, to produce a mixture of epimers having the formula

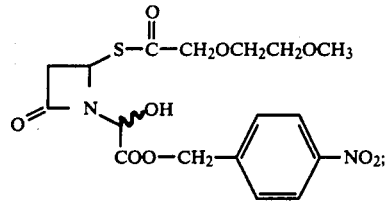

(c) converting the so-produced hydroxy intermediate III to the corresponding chloro epimeric mixture of the formula

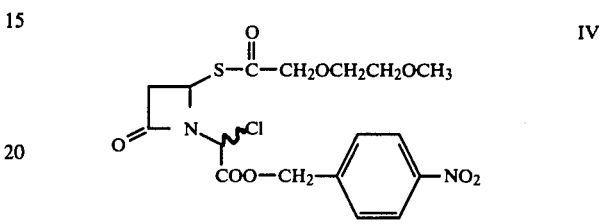

by treatment with a chlorinating agent in an inert organic solvent in the presence or absence of a base; and (d) reacting the chloro intermediate IV with a phosphine compound of the formula

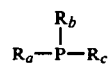

wherein $R_a$, $R_b$ and $R_c$ are phenyl or $C_1-C_6$ alkyl, preferably phenyl, in an inert organic solvent in the presence of a base to produce the desired phosphorane intermediate II.

The nucleophilic displacement of the acetoxy group in step (a) may be conducted according to the general procedure of Clauss et al. in Liebigs Ann. Chem. 1974, 539–560. The 4-acetoxy-2-azetidinone is reacted with approximately an equimolar amount of the 2-methoxyethoxythioacetic acid in an inert solvent (e.g. water, methanol, ethanol) in the presence of a base such as an alkali metal hydroxide or alkoxide. Good results are obtained when the reactants are added under ice-bath conditions and the stirred reaction is then allowed to warm to room temperature.

Reaction step (b) is carried out in a suitable inert organic solvent such as benzene or toluene with p-nitrobenzyl glyoxylate or a reactive oxo-derivative thereof such as p-nitrobenzyl glyoxylate hydrate. The reaction is preferably carried out at elevated temperatures (e.g. 50°–150° C.), most preferably under reflux conditions. When a hydrate of the ester is used, resulting water may be removed azeotropically or with molecular sieves. The hydroxy ester product III is formed as a mixture of epimers which may be optionally purified by chromatography or used directly in the next step.

The chloro ester intermediate IV is next formed by reacting intermediate III in an inert organic solvent (e.g. tetrahydrofuran, dioxane, or a mixture thereof) in the presence or absence of a base, preferably an organic base such as an aliphatic tertiary amine (e.g. triethylamine) or a heterocyclic tertiary amine (e.g. pyridine or collidine), with a cholorinating agent capable of converting a hydroxy group to a chloro group such as $SOCl_2$, $POCl_3$ or $PCl_5$. Preferred temperatures for this step are room temperature for the case when a base is not employed to about 0° to −10° C. when a base is present. Where the chlorinating agent used is itself an inert solvent under the reaction conditions of step (c), e.g. SOCl₂, the reaction may be carried out without the use of a separate solvent. Product IV is obtained as a mixture of epimers which may optionally be purified by chromatography before use in step (d).

Intermediate IV is converted to the phosphorane intermediate II by reaction with triphenylphosphine or a tri(lower)alkylphosphine such as tri-n-butylphosphine in an organic solvent (e.g. an aliphatic, cycloaliphatic or aromatic hydrocarbon such as hexane, cyclohexane, benzene or toluene or an ether such as dioxane or tetrahydrofuran, or a mixture thereof) in the presence of a base, preferably an organic tertiary amine such as triethylamine, pyridine or 2,6-lutidine. The reaction may be carried out at temperatures from room temperature up to the reflux temperature of the solvent system. Intermediate II may be optionally purified by chromatography before being used as the starting material for preparation of compound I.

The free acid compound of formula I in the form of the racemic mixture or resolved dextrorotatory optical isomer and pharmaceutically acceptable salts and physiologically cleavable esters of said acid have been found to be potent broad-spectrum antibacterial agents useful in the treatment of infectious diseases in animals, including man, caused by both Gram-positive and Gram-negative organisms. The compounds are also of value as nutritional supplements in animal feeds and as agents for the treatment of mastitis in cattle. In addition, the active compounds of the invention possess good β-lactamase resistance and show advantageously high blood serum levels upon oral or parenteral administration.

The active compounds provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the active compounds of this invention may be administered orally or parenterally in an amount of from about 5 to 200 mg./kg./day and preferably about 5 to 20 mg./kg./day in divided dosage, e.g. three or four times a day. They are administered in dosage units containing, for example, 125, 250 or 500 mg. of active ingredient with suitable physiologically acceptable carriers or diluents.

The present invention also provides a method of combatting bacterial infections in animals, particularly warm-blooded animals, which comprises administering an acid of formula I or a physiologically cleavable ester thereof or a pharmaceutically acceptable salt thereof, either in the form of a racemic mixture or preferably a dextrorotatory isomer, or a pharmaceutical composition thereof, to an infected host in an amount sufficient to combat such infection.

Illustrative examples of the preparation of starting materials and compounds of the present invention follow. These examples are given in illustration of, but not in limitation of, the present invention. All temperatures are in degrees Celsius. Unless otherwise indicated, the products of Examples 1-6 are racemic mixtures.

Preparation of Starting Materials

Preparation 1: 2-Methoxyethoxyacetic acid

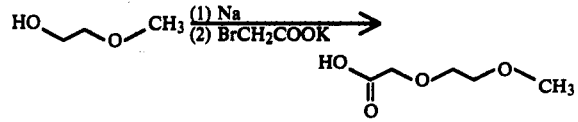

Sodium (1.15 g.; 50.0 mmoles) was dissolved in 2-methoxyethanol (50 ml.; anhydrous) under N₂ at room temperature. The temperature rose to 110° over about a 30 minute period. The pale yellow mixture was cooled to room temperature and to this was added powdered potassium bromoacetate (8.85 g.; 50.0 mmoles) under vigorous stirring. The mixture (suspension) was stirred at room temperature overnight (19 hrs.) under N₂. The excess of methoxyethanol was removed in vacuo and the residue diluted with H₂O (50 ml.) and neutralized with 1N HCl (50 ml.). After evaporation of water, the residue was extracted with CH₂Cl₂(75 ml.×2) and the extracts were evaporated to dryness yielding 5.26 g. of yellowish oil. This oil was distilled under reduced pressure, yielding 2-methoxyethoxyacetic acid (4.72 g.; 35.2 mmoles; yield 70.5%) as a colorless oil: b.p. 98° C./0.3 mm Hg; nmr (CDCl₃): δppm 3.45 (3H, s, -OCH₃), 3.4-3.9 (4H, m, —OCH₂CH₂O-), 4.22 (2H, s, HO₂CCH₂O-), 9.74 (1H, br. s., -CO₂H); ir (neat) 1750 cm⁻¹ ($\nu_{c=o}$—CO₂H).

Preparation 2: 2-Methoxyethoxyacetyl chloride

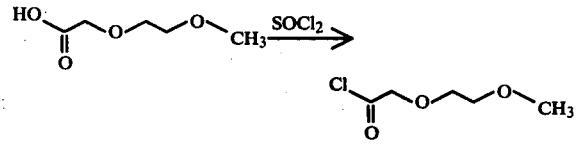

To 2-methoxyethoxyacetic acid (670 mg.; 4.00 mmoles) was added at 0°-2° under N₂ atmosphere, SOCl₂ (5ml.). The mixture was stirred at room temperature under N₂ for 2 hours. Excess SOCl₂ was evaporated and the residue was diluted with dry benzene (15 ml.), evaporated again, and dried over NaOH (in vacuo) to yield 2-methoxyethoxyacetyl chloride (705 mg.; 4.62 mmoles; yield 92.5%) as a colorless liquid. nmr (CDCl₃): δppm 3.40 (3H, s, -OCH₃), 3.4-3.9 (4H, m, -CH₂CH₂-), 4.56 (2H, s, ClOCH₂O-); ir (neat): 1810 cm⁻¹ ($\nu_{c=o}$, acid chloride).

Preparation 3: 2-Methoxyethoxythioacetic acid

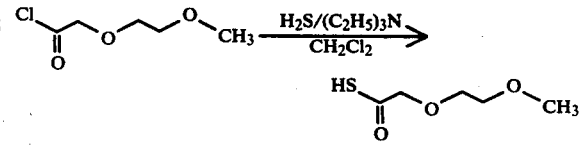

A solution of 2-methoxyethoxyacetyl chloride (700 mg.; 4.59 mmoles) in methylene chloride (10 ml.; dried over molecular sieves) was added dropwise at 0°-5° to a stirred solution of triethylamine (0.7 ml.; 508 mg.; 5.04 mmoles) in methylene chloride (20 ml.) which had been saturated at 0°-5° with H₂S (ca. 30 min.). The light yellow mixture was stirred at 0°-5° for 30 min. and then at room temperature for 30 min. The mixture was washed with 1N HCl (10 ml.×2) and then brine. The CH₂Cl₂ layer was dried (Na₂SO₄) and evaporated yielding 2-methoxyethoxythioacetic acid (480 mg.; 3.20 mmoles; yield 69.7%) as a light yellow liquid: nmr (CDCl₃): δppm 3.42 (3H, s, —OCH₃), 3.4–3.9 (4H, m, —CH₂CH₂-), 4.10 (2H, s, -OCCH₂O), 5.0 (1H, br, -COSH); ir (neat): 2550 cm⁻¹ ($v_{S-H}$), 1770 ($v_{c=o}$, thio acid).

Preparation 4:
4-(2-Methoxyethoxythioacetoxy)-2-azetidinone

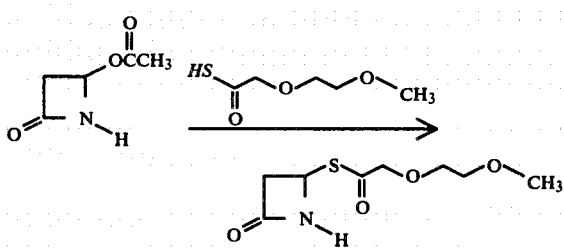

To a solution of 2-methoxyethoxythioacetic acid (990 mg.; 6.60 mmoles) in 1N KOH (6.0 ml.) and water (30 ml.) was added in an ice-bath under nitrogen atmosphere 4-acetoxy-2-azetidinone (777 mg.; 6.00 mmoles). The reaction mixture was stirred at room temperature (N₂) for 1 hr. and then extracted with methylene chloride (30 ml.×3). The extracts were washed with brine, dried (Na₂SO₄) and evaporated yielding 4-(2-methoxyethoxythioacetoxy)-2-azetidinone (1.26 g.; 5.76 mmoles; 96% yield) as a yellow oil. nmr (CDCl₃): δppm 2.8–3.8 (2H, m, H-3), 3.40 (3H, s, -OCH₃), 3.4–3.9 (4H, m, -CH₂CH₂-O), 4.25 (2H, s, O=CCH₂O-), 5.25 (1H, dd, $J_{3-4\ cis}$=5 Hz, $J_{3-4\ trans}$=3 Hz, H-4), 7.3 (1H, br.s, -NH); ir (neat): 3280 cm⁻¹ ($v_{N-H}$), 1770 ($v_{c=o}$, β-lactam), 1690 ($v_{c=o}$, thioester).

EXAMPLE 1 p-Nitrobenzyl 2-(2-Methoxyethoxymethyl)penem-3-carboxylate

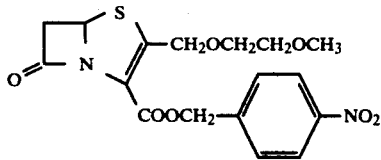

(A) Preparation of p-Nitrobenzyl 2-[4-(2-Methoxyethoxyacetylthio)-2-oxo-1-azetidinyl]-2-hydroxyacetate

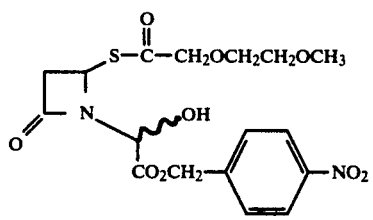

A mixture of 4-(2-methoxyethoxythioacetoxy)-2-azetidinone (381 mg.; 1.74 mmole) and p-nitrobenzyl glyoxylate hydrate (500 mg.; 2.20 mmoles) in benzene (30 ml.) was heated at reflux with a Dean-Stark trap filled with 4 A molecular sieves for 18 hours. Evaporation of the solvent gave the title product (820 mg.) as an oil. nmr (CDCl₃): δppm 2.8–3.9 (2H, m, H-3), 3.47–3.49 (3H, s, -OCH₃), 3.5–3.9 (4H, m, -OCH₂CH₂O-), 4.19–4.24 (2H, s, O=C-CH₂O-), 5.3–5.7 (5H, mixture of H-4, -CHOH, -CH₂-Ar), 7.49, 7.65, 8.20, 8.35 (4H, A₂' B₂' type, aromatic -H); ir (neat): 3350 cm⁻¹ ($v_{OH}$), 1770 broad, $v_{c=o}$, β-lactam and ester), 1965 ($v_{c=o}$, thioester), 1525 ($v_{NO_2}$).

(B) Preparation of p-Nitrobenzyl 2-[4-(2-Methoxyethoxyacetylthio)-2-oxo-1-azetidinyl]-2-chloroacetate

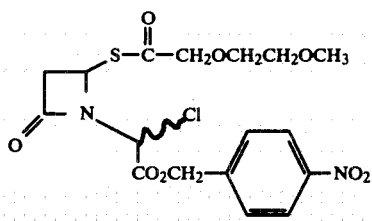

To 800 mg. of p-nitrobenzyl 2-[4-(2-methoxyethoxyacetylthio)-2-oxo-1-azetidinyl]-2-hydroxyacetate was added (all at once) at 0° under N₂ atmosphere, thionyl chloride (3 ml.) and the mixture was stirred at room temperature under N₂ for 1 hour. The excess of thionyl chloride was removed in vacuo and the residue dissolved in dry benzene (10 ml.) and evaporated to dryness. There was obtained the title product (791 mg.) as a yellowish oil. nmr (CDCl₃): δppm 2.9–3.9 (2H, m, H-3), 4.10 (3H, s, -OCH₃), 3.5–3.9 (4H, m, -OCH₂C-H₂O-), 4.24 (2H, s, O=C-CH₂O-), 5.35–5.45 (2H, m, -CH₂-Ar), 5.70 (1H, m, H-4), 6.12 (1H, s, -CHCl), 7.52, 7.67, 8.21, 5.39 (4H, A₂' B₂', aromatic -H); ir (neat): 1780 cm⁻¹ (broad, $v_{c=o}$, β-lactam and ester), 1695 ($v_{c=o}$, thioester), 1525 ($v_{NO_2}$).

(C) Preparation of p-Nitrobenzyl 2-[4-(2-Methoxyethoxyacetylthio)-2-oxo-1-azetidinyl]-2-triphenylphosphoranylideneacetate

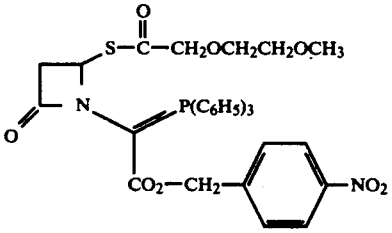

A mixture of p-nitrobenzyl 2-[4-(2-methoxyethoxyacetylthio)-2-oxo-1-azetidinyl]-2-chloroacetate (761 mg.), triphenylphosphine (524 mg.; 2.00 mmoles) and 2,6-lutidine (0.235 ml.; 214 mg.; 2.00 mmoles) in tetrahydrofuran (7 ml.) was stirred under N₂ atmosphere at room temperature for 50 hours. After filtration of the precipitate, the filtrate was evaporated to yield 1.39 g. of a crude oil. This oil was purified by columm chromatography (SiO₂; 30 g.; eluant-ethyl acetate) yielding title product (494 mg.; 0.736 mmole; yield 42.3% based on starting ester) as a brownish oil.

(D) Preparation of p-Nitrobenzyl 2-(2-Methoxyethoxymethyl)-penem-3carboxylate A solution of the phosphorane product from step C (494 mg.; 0.736 mmole) in toluene (50 ml.) was heated at reflux for 4 hours and, after cooling, the insoluble material was removed. Evaporation of the filtrate gave 498 mg. of oily solid which was purified by column chromatography ($SiO_2$; 15 g.; eluant-diethyl ether:benzene (1:9 v/v)) yielding the title product (133 mg.; 0.338 mmole; yield 46%) as an oil. nmr ($CDCl_3$) $\delta$ppm 3.39 (3H, s, -$OCH_3$), 3.4–3.8 (4H, m, $OCH_2CH_2O$), 3.86 (1H, AB of ABX type, $J_{6-6}=17$ Hz, $J_{5-6\ cis}=4$ Hz, H-6), 4.77 (2H, AB type, $J_{AB}=16$ Hz, $C_3$-$CH_2O$-), 5.34 (2H, AB type, $J_{AB}=14$ Hz, -$OCH_2$-Ar), 5.69 (1H, X of ABX type, $J_{5-6\ cis}=4$ Hz, $J_{5-6\ trans}=2$ Hz, H-5), 7.22, 7.70, 8.17, 8.32 (4H, $A_2'$ $B_2'$, aromatic H); ir (neat): 1790 cm$^{-1}$ ($\nu_{c=o}$, $\beta$-lactam), 1710 ($\nu_{c=o}$, ester), 1525 ($\nu_{NO_2}$); UV ($C_2H_5OH$) $\lambda_{max}$ 264 m$\mu$ ($\epsilon=1.3\times10^4$), 321 m$\mu$ ($\epsilon=9.8\times10^3$).

EXAMPLE 2

Sodium 2-(2-Methoxyethoxymethyl)penem-3-carboxylate

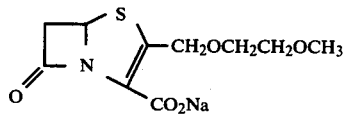

A mixture of p-nitrobenzyl 2-(2-methoxyethoxymethyl)-penem-3-carboxylate (133 mg.; 0.338 mmole) in tetrahydrofuran (12 ml.), diethylether (24 ml.) and $NaHCO_3$ (28.4 mg.; 0.338 mmole) in $H_2O$ (12 ml.) was shaken on a Parr hydrogenator for 3.5 hr. at 30 p.s.i. $H_2$ using 30% Pd on Celite (diatomaceous earth; 135 mg.) as catalyst. The catalyst was removed and washed with diethyl ether and water. The aqueous layer after being washed with diethyl ether was lyophilized to yield the title salt (68 mg.; 0.24 mmole; yield 72%) as yellow powder. nmr ($D_2O$), 3.84 (3H, s, -$OCH_3$), 3.8–4.5 (2H, AB of ABX type, H-6), 4–4.3 (4H, m, -$OCH_2CH_2O$-), 5.17 (2H, AB type, $J_{AB}=14$ Hz, $C_3$-$CH_2O$-), 6.18 (1H, X of ABX type, $J_{5-6\ cis}=4$ Hz, $J_{5-6\ trans}=2$ Hz, H-5); ir (KBr disc): 1765 cm$^{-1}$ ($\nu_{c=o}$, $\beta$-lactam); UV ($H_2O$)$\lambda_{max}$ 254 m$\mu$ ($\epsilon=3.3\times10^3$), 305 m$\mu$ ($\epsilon=4.6\times10^3$).

Substitution of an equivalent weight of $KHCO_3$ in the above procedure for the $NaHCO_3$ used therein gives the corresponding potassium salt.

EXAMPLE 3

2-(2-Methoxyethoxymethyl)penem-3-carboxylate

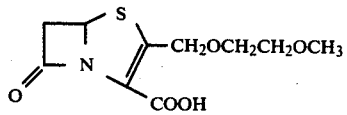

The procedure of Example 2 is repeated except that the aqueous layer after being washed with diethyl ether is acidified to pH 2-2.5 with cold 1% HCl and extracted with ethyl acetate. The organic extract is then washed with brine and dried over $Na_2SO_4$ to give the title product.

EXAMPLE 4

Resolution of d,l-2-(2-Methoxyethoxymethyl)penem-3-carboxylate

A.
(+)-2-(2-Methoxyethoxymethyl)penem-3-carboxylic Acid

To a suspension of crude d,l-2-(2-methoxyethoxymethyl)penem-3-carboxylic acid in isopropanol is added with stirring an equimolar weight of d-(+)-α-methylbenzylamine. The mixture is allowed to stand at room temperature for 0.5 hrs. The solid is removed by filtration, recrystallized from methanol and converted to free acid by treatment with cold 1N HCl. Extraction with $CHCl_3$ gives the title isomer.

B.
(−)-2-(2-Methoxyethoxymethyl)-penem-3-carboxylic Acid

To a hot solution of crude d,l-2-(2-methoxyethoxymethyl)penem-3-carboxylic acid in isopropanol is added a solution of an equimolar weight of l-(−)-α-methylbenzylamine in isopropanol. The solution is allowed to crystallize at room temperature. The crystalline solid is separated by filtration, recrystallized from $CH_3OH$ and treated with cold 1N HCl. Upon extraction with $CHCl_3$, the levorotatory free acid product is obtained.

EXAMPLE 5

(+)-Sodium 2-(2-Methoxyethoxymethyl)penem-3-carboxylate

To a solution of (+)-2-(2-methoxyethoxymethyl)-penem-3-carboxylic acid in methanol is added one equivalent of sodium ethylhexanoate. There is produced the title salt.

Substitution of potassium ethylhexanoate in the above procedure gives (+)-potassium 2-(2-methoxyethoxymethyl)penem-3-carboxylate.

Treatment of (+)-2-(2-methoxyethoxymethyl)-penem-3-carboxylic acid with other pharmaceutically acceptable bases in a suitable solvent gives the corresponding pharmaceutically acceptable carboxylic acid salts.

EXAMPLE 6

(+)-Pivaloyloxymethyl 2-(2-Methoxyethoxymethyl)penem-3-carboxylate

A mixture of (+)-2-(2-methoxyethoxymethyl)penem-3-carboxylic acid in dimethylformamide is treated with one equivalent of triethylamine and stirred to effect solution. Bromomethyl pivalate (1 equivalent) in dimethylformamide is then added. The resulting solution is stirred at room temperature. The mixture is then clarified by filtration and the filtrate poured into ice water. The separated solid is filtered, washed with water and dried to give the title ester.

The respective acetoxymethyl, methoxymethyl, acetonyl and phenacyl esters of (+)-2-(2-methoxyethoxymethyl)penem-3-carboxylic acid may be prepared by substituting in the method above for the bromomethyl pivalate used therein an equimolar weight of chloromethyl acetate, chloromethyl methyl ether, chloroacetone and phenacyl bromide, respectively.

Biological Activity Data

The in vitro minimum inhibitory concentrations (MIC) of d,l-2-(2-methoxyethoxymethyl)penem-3-carboxylic acid (as the sodium salt) were determined for a number of microorganisms as determined by overnight incubation at 37° C. by tube dilution. Ampicillin was included as a comparison compound. MIC data for the compounds are shown in the following table.

| | M.I.C. in mcg./ml. | |
|---|---|---|
| Organism | d,l-2-(2-methoxy-ethoxymethyl)penem-3-carboxylic acid | Ampicillin |
| Str. pneumoniae A9585 | .03 | .004 |
| Str. pyogenes A9604 | .13 | .004 |
| Staph. aureus A9537 | .5 | .03 |
| Staph. aureus +50% serum A9537 | 8 | .06 |
| Staph. aureus A9606 | 16 | >125 |
| Staph. aureus A15097 | 16 | 32 |
| Str. faecalis A20688 | 63 | .25 |
| E. coli A15119 | 1 | 1 |
| E. coli A20341-1 | >125 | >125 |
| K. pneumoniae A15130 | 32 | 125 |
| K. species A20468 | >125 | >125 |
| Pr. mirabilis A9900 | 1 | .13 |
| Pr. vulgaris A9716 | 1 | .25 |
| Pr. morganii A15153 | 2 | 125 |
| Prov. stuartii A21205 | 2 | 16 |
| Ser. marcescens A20019 | 8 | 16 |
| Ent. cloacae A9659 | 8 | 63 |
| Ent. cloacae A9656 | 8 | 125 |
| Ps. aeruginosa A9843A | >125 | >125 |
| Ps. aeruginosa A21213 | >125 | >125 |

We claim:
1. A compound of the formula

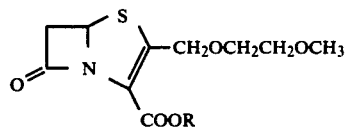

wherein R is hydrogen or an easily removable ester protecting group, or a pharmaceutically salt thereof.

2. A compound according to claim 1 having the formula

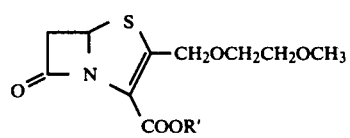

wherein $R^1$ is p-nitrobenzyl or the residue of a physiologically cleavable ester group.

3. A compound according to claim 2 wherein $R^1$ is p-nitrobenzyl.

4. A compound according to claim 2 wherein $R^1$ is the residue of a physiologically cleavable ester group.

5. A compound according to claim 2 wherein $R^1$ is indanyl, phthalidyl, methoxymethyl or acyloxymethyl of the formula

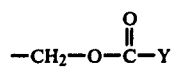

in which Y is $C_1$–$C_4$ alkyl or phenyl.

6. A compound according to claim 2 wherein $R^1$ is methoxymethyl, pivaloyloxymethyl, acetoxymethyl, phthalidyl or indanyl.

7. The acid of claim 1 having the formula

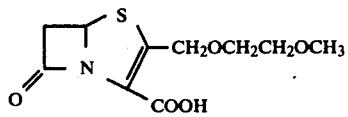

or a pharmaceutically acceptable salt thereof.

8. The acid of claim 7, said acid being 2-(2-methoxyethoxymethyl)penem-3-carboxylic acid.

9. The sodium salt of the acid of claim 7.

10. The potassium salt of the acid of claim 7.

11. The dextrorotatory optical isomer of the compound having the formula

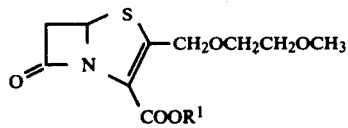

wherein $R^1$ is hydrogen or the residue of a physiologically cleavable ester group or, when $R^1$ is hydrogen, a pharmacutically acceptable salt thereof, said isomer being substantially free of the corresponding levorotatory optical isomer.

12. The compound of claim 11 wherein $R^1$ is indanyl, phthalidyl, methoxymethyl or acyloxymethyl of the formula

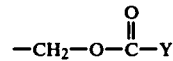

in which Y is $C_1$–$C_4$ alkyl or phenyl.

13. The compound of claim 11 wherein $R^1$ is methoxymethyl, pivaloyloxymethyl, acetoxymethyl, phthalidyl or indanyl.

14. The acid of claim 11 having the formula

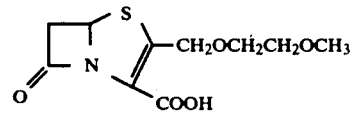

or a pharmaceutically acceptable salt thereof.

15. The acid of claim 11, said acid being (+)-2-(2-methoxyethoxymethyl)penem-3-carboxylic acid.

16. The sodium salt of the acid of claim 11.

17. The potassium salt of the acid of claim 11.